(12) United States Patent
Hanson et al.

(10) Patent No.: US 6,348,337 B1
(45) Date of Patent: Feb. 19, 2002

(54) PROCESS FOR THE PREPARATION OF C-4 DEACETYLTAXANES

(75) Inventors: Ronald L. Hanson, Morris Plains; Ramesh N. Patel, Bridgewater, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/641,176

(22) Filed: Aug. 17, 2000

Related U.S. Application Data

(63) Continuation of application No. 09/360,948, filed on Jul. 27, 1999, now abandoned.
(60) Provisional application No. 60/097,028, filed on Aug. 18, 1998, and provisional application No. 60/119,938, filed on Feb. 12, 1999.

(51) Int. Cl.$^7$ ............................ C12P 17/00; C12P 17/02
(52) U.S. Cl. .................. 435/123; 435/117; 435/195
(58) Field of Search ............................... 435/117, 123, 435/195

(56) References Cited

U.S. PATENT DOCUMENTS

| | | | |
|---|---|---|---|
| 5,516,676 A | 5/1996 | Hanson et al. | 435/119 |
| 5,547,866 A | 8/1996 | Durzan et al. | 435/123 |
| 5,739,359 A | 4/1998 | Kingston et al. | 549/358 |
| 5,773,461 A | 6/1998 | Wittman et al. | 549/510 |

OTHER PUBLICATIONS

Chen, Tetrahedron Letters, vol. 37, No. 23, pp. 3935–3938, 1996.

Yuan et al, "Synthesis of 6α–Hydroxypaclitaxel, the Major Human Metabolite of Paclitaxel", Tetrahedron Letters, 29 (1998) 4967–4970.

Georg et al, "Selecective C–2 and C–4 Deacylation and Acylation of Taxol: The First Synthesis of a C–4 Substituted Taxol Analogue", Tetrahedron Letters, vol. 35, No. 48, pp. 8931–8934, 1994.

Chen et al, "First Syntheses of Novel Paclitaxel (Taxol) Analogs Modified at the C4–Position", J. Org. Chem. 1994, 59, 6156–6158.

Chen et al, "Synthesis and Biological Evaluation of C–13 Amide–Linked Paclitaxel (Taxol) Analogs", J. Org. Chem. 1996, 61, 2065–2070.

Chen et al, "Novel C–4 Paclitaxel (Taxol®) Analogs: Potent Antitumor Agents", Bioorganic & Medicinal Chemistry Letters, vol. 5, No. 22, pp. 2741–2746, 1995.

Samaranayake et al, "Modified Taxols, 8 Deacylation and Reacylation of Baccatin III", Journal of Natural Products, vol. 56, No. 6, pp. 884–898, Jun. 1993.

Uoto et al, "A New Method to Modify the C–4 Position of 10–Deacetylbaccatin III", Chem. Pharm. Bull. 45(12) pp. 2093–2095 (1997).

Kim et al, "Migration Between C–2 and C–4 Hydroxyl Groups in Paclitaxel Core", Korean J. of Med. Chem., vol. 7, No. 1, 1997.

Py et al, "A novel rearrangement of the taxane skeleton", Bull.Soc. Chim. Fr. (1993) 130, 189–191.

Primary Examiner—Herbert J. Lilling
(74) Attorney, Agent, or Firm—Gabriel Lopez

(57) ABSTRACT

A process useful for the preparation of intermediates in synthesis or semi-synthesis of paclitaxel analogs wherein a starting taxane such as 10-deacetylbaccatin III is deacetylated at the C-4 position using a microorganism or an enzyme derived therefrom to provide 4-deacetyltaxanes, such as 4,10-dideacetylbaccatin III.

5 Claims, 2 Drawing Sheets strain SC16250
10% w/v
50 mM KPi pH 7
0.2 mg/ml 10-DAB

PROCESS FOR THE PREPARATION OF C-4 DEACETYLTAXANES

This application is a continuation of 09/360,948 filed Jul. 27, 1999, now abandoned, which claims priority benefit under Title 35 §119(e) of United 5 States Provisional Application Nos. 60/097,028, filed Aug. 18, 1998, and 60/119, 938, filed Feb. 12, 1999, both which are entitled "Process for the Preparation of C-4 Deacetyltaxanes, the entire contents of which are incorporated herein by reference.

BRIEF DESCRIPTION OF THE INVENTION

The present invention is directed to a process using microorganisms or enzymes derived therefrom for deacetylation of taxanes at C-4 to give 4-deacetyltaxanes, useful intermediates for the synthesis of new anti-cancer agents.

BACKGROUND OF THE INVENTION

Taxanes are diterpene compounds which find utility in the pharmaceutical field. For example, taxanes containing aryl heterocyclic or cycloalkyl groups on the C-13 sidechain find utility as anti-cancer agents. Taxanes include pacltitaxel, cephalomannine, taxol c, 10-deacetylpaclitaxel, 10-deacetylcephalomannine, 7-β-xylosylpaclitaxel, baccatin-III, 10-deacetylbaccatin III, 7-β-xylosyl-10-deacetyl cephalomannine, 7-β-xylosyl-10-deacetylbaccatin III, 7-β-xylosylbaccatin III, and 10-deacetyl-taxol c.

Paclitaxel (Taxol), a diterpene taxane compound, is a natural product extracted from the bark of the Pacific yew tree, Taxus Brevifolia. It has been shown to have excellent antitumor activity in in vivo animal models, and recent studies have elucidated its unique mode of action, which involves abnormal polymerization of tubulin and disruption of mitosis during the cell cycle. Taxol has recently been approved for the treatment of refractory advanced ovarian cancer, breast cancer, non-small cell lung cancer, and most recently, AIDS-related Kaposi's Sarcoma. The results of paclitaxel clinical studies are replete in scientific periodicals and have been reviewed by numerous authors, such as Rowinsky and Donehower in "The Clinical Pharmacology and Use of Antimicrotubule Agents in Cancer Chemotherapeutics", *Phamac. Ther.*, 52, pp. 35–84 (1991); Spencer and Faulds, Paclitaxel, A Review of its Pharmacodynamic and Pharmacokinetic Properties and Therapeutic Potential in the Treatment of Cancer, *Drugs*, 48 (5), pp. 794–847 (1994); K. C. Nicolau et al., Chemistry and Biology of Taxol, *Angew. Chem., Int. Ed. Eng.*, 33, pp. 15–44 (1994); F. A. Holmes, A. P. Kudelka, J. J. Kavanaugh, M. H. Huber, J. A. Ajani, and V. Valero, "Taxane Anticancer Agents—Basic Science and Current Status", edited by Gunda I. Georg, Thomas C. Chen, lwao Ojima, and Dolotrai M. Vyas, pp. 31–57 American Chemical Society, Wash., D.C. (1995); Susan G. Arbuck and Barbara Blaylock, "Taxol( Science and Applications", edited by Matthew Suffness, pp. 379–416, CRC Press, Boca Raton, Fla. (1995) and the references cited therein.

The structure of Taxol® is shown below along with the conventional numbering system for molecules belonging to the Taxane class; such numbering system is also employed in this application.

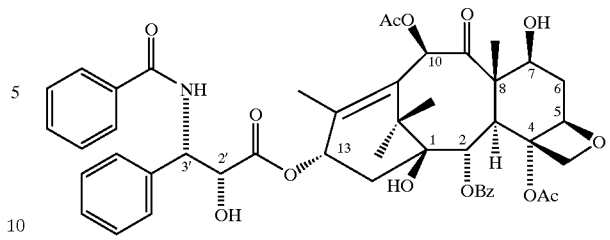

With reference to the numbering of the taxane, reference to a particular carbon on the taxane structure shall be indicated throughout this application by a "C-number", which signifies the carbon on the taxane according to the above numbering system. For example, "C-13" refers to the carbon at position 13 on the taxane ring as shown above, having a sidechain coupled thereto.

The central backbone structural unit of paclitaxel is baccatin III, a diterpenoid having the chemical structure:

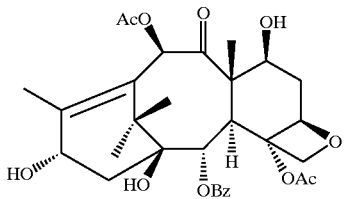

It is also very similar in structure to 10-deacetylbaccatin III ("10-DAB III"), which has the chemical structure:

but which lacks an acetate ester at the 10-position alcohol.

Chemical modification of the paclitaxel structure at C-4 and other positions has been explored by many groups to determine structure/activity relationships and to try to obtain compounds with superior efficacy to taxol to develop as second generation drugs. See U.S. Pat. No. 5,773,461; Gunda I. George, Syed M. Ali, Thomas C. Boge, Apurba Datta, and Lise Falborg, "Selective C-2 and C-4 Deacylation of Taxol: The First Synthesis of a C-4 Substituted Taxol Analogue", *Tetrahedron Let.*, 35:48, pp. 8931–8934 (1994); Shu-Hui Chen, John F. Kadow, Vittorio Farina, Craig R. Fairchild and Kathy A. Johnston, "First Synthesis of Novel Paclitaxel (Taxol) Analogs Modified at the C-4 Position", *J. Org. Chem.* 59, pp. 6156–6158 (1994); S. Py, and F. Khuong-Huu, "A Novel Rearrangement of The Taxane Skeleton", *Bull. Soc. Chim. Fr.*, 130, pp. 189–191 (1993).

Replacement of the C-4-acetyl group of paclitaxel with other substituents has lead to compounds with improved potency in activity assays (S. Chen et al., Biorganic and Medicinal Chemistry Letters, 5:2741–2748 (1995)). An enzyme capable of specifically removing the C-4-acetyl group from taxanes will be useful in the synthesis of C-4-modified paclitaxel analogs to provide starting material to allow incorporation of other groups at this position, for example C-4 butyrate esters, C-4 cyclobutyl esters, C-4 propyl esters, C-4 cyclopropyl esters and C-4 methyl and ethyl carbonates.

DESCRIPTION OF THE INVENTION

Figure 1:
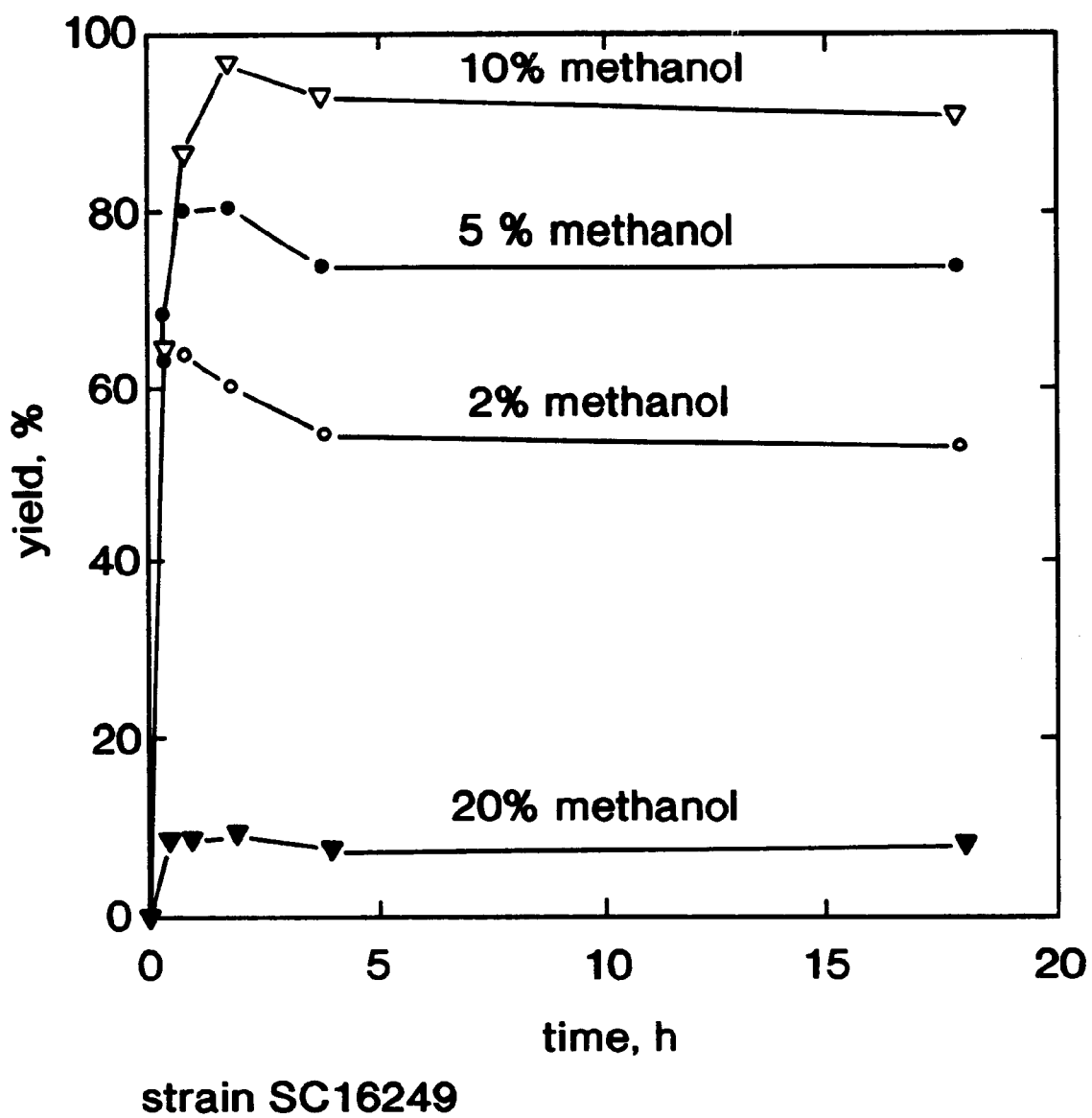
FIG. 1 illustrates the effect of methanol concentration on the C-4 deacetylation by strain SC16249.
Figure 2:
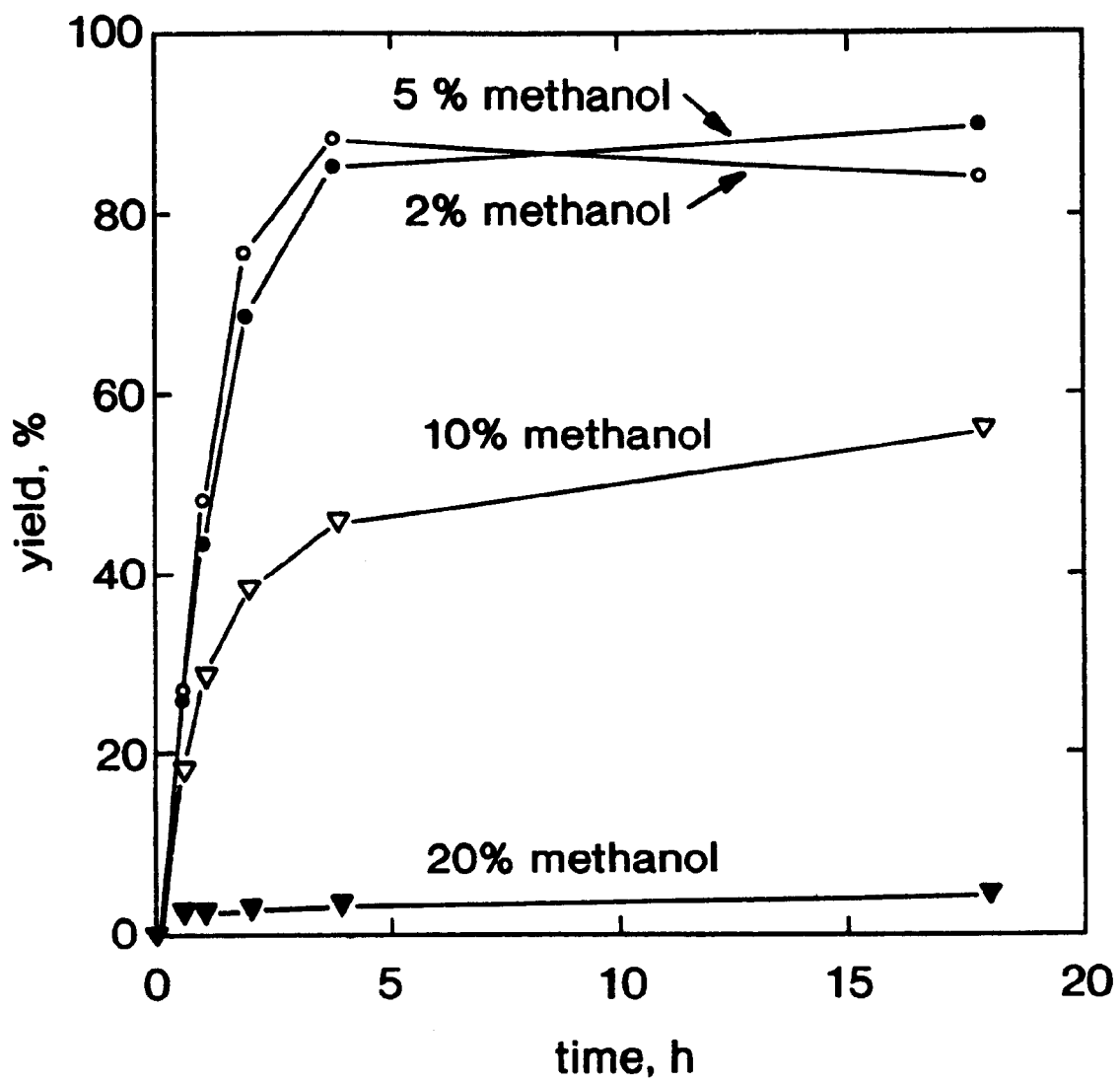
FIG. 2 illustrates the effect of methanol concentration on the C-4 deacetylation by strain SC16250.

It is an object of the present invention to provide a new, useful and efficient protocol for the preparation of 4-deacetyltaxanes.

Another object of the present invention is the provision of a process using microorganisms or enzymes derived therefrom for deacetylation of taxanes at the C-4 position to provide 4-deacetyltaxanes.

An additional object of the present invention is the provision of a simple, efficient, and cost effective protocol for the provision of second-generation taxol analogues having various substituents at the C-4 position.

Accordingly, the present invention encompasses a novel method by which 10-deacetyl baccatin III can be efficiently converted to 4,10-dideacetylbacatin III using a microorganism or one or more enzymes derived from the microorganism. The resulting 4,10-dideacetylbacatin III compound may then be utilized as part of novel processes for the synthesis and semi-synthesis of paclitaxel analogs.

The present disclosure is broadly directed to a process for the efficient deacetylation of 10-DAB III at the C-4 position. The deacetylation at C-4 transpires as a result of a biotransformation caused by a microorganism or an enzyme derived from said microorganism. More specifically, the present invention is directed to the use of an organism that transforms 10-DAB III into 4,10-dideacetylbaccatin III.

The terms "enzymatic process" or "enzymatic method", as used herein, denote a process or method of the present invention employing an enzyme or microorganism. Use of "an enzyme or microorganism" in the present method includes use of a single, as well as two or more, enzymes or microorganisms.

The term "taxane", as used herein, denotes compounds having a taxane moiety as described following. The term "taxane moiety", as used herein, denotes moieties containing the core structure (with numbering of ring system positions used herein shown):

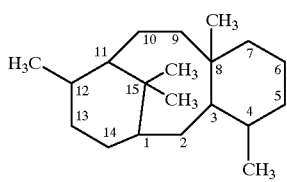

which core structure may be substituted and which may contain ethylenic unsaturation in the ring system thereof. Such moieties having an oxetane ring fused at the 4- and 5- positions, such as is found in paclitaxel, are preferred.

The enzyme or microorganism employed in the present invention may be any enzyme or microorganism capable of catalyzing the enzymatic hydrolysis described herein. The enzymatic or microbial materials, regardless of origin or purity may be employed in the free state or immobilized on a support such as by physical adsorption or entrapment.

Exemplary microorganisms, which have been identified through a screening process, include Rhodococcus sp. ATCC 202192 (SC 16249) and Rhodococcus sp. ATCC 202191 (SC 16250). The term "ATCC" as used herein refers to the accession number of the American Type Culture Collection, 10801 University Blvd., Manassas, Va., the depository for the organism referred to. The above microorganisms ATCC 202192 and ATCC 202191 were deposited on Jan. 14, 1999. The term "SC" denotes the designation given to the microorganism as part of the Squibb culture collection.

It should be understood that mutants of the biologically pure microorganisms ATCC 202192 (SC 16249), and ATCC 202191 (SC 16250) are also contemplated by the present invention for use in the biotransformation described herein, such as those modified by the use of chemical, physical (for example, x-rays) or biological means (for example, molecular biology techniques).

Rhodococcus sp. ATCC 202192 (SC 16249) and Rhodococcus sp. ATCC 202191 (SC 16250) may be cultivated on a medium of 0.5% toasted nutrisoy, 2% glucose, 0.5% yeast extract 0.5% $K_2HPO_4$, 0.5% NaCl, adjusted to pH 7 with HCl. The organisms were isolated from soil (from a sample from Parsippany, N.J.), and are gram positive, non-motile rods with an aerobic requirement Preferred enzymes include those derived from microorganisms, particularly those microorganisms described above. Enzymes may be isolated, for example, by extraction and purification methods, such as ion exchange chromatography, followed by hydrophobic interaction chromatography and gel filtration. The present invention further provides the enzymes capable of the present hydrolysis which may be isolated from Rhodococcus sp. ATCC 202192 (SC 16249) and Rhodococcus sp. ATCC 202191 (SC 16250), for example by the above techniques.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. Escherichia coli, modified to contain a gene or genes for expressing one or more enzymes capable of catalysis as described herein.

Where one or more microorganisms are employed, the enzymatic deacetylation process of the present invention may be carried out subsequent to the fermentation of the microorganism (two-stage fermentation and hydrolysis), or concurrently therewith, that is, in the latter case, by in situ fermentation and hydrolysis (single-stage fermentation and hydrolysis).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements may include magnesium, manganese, calcium, cobalt, nickel, iron, sodium and potassium salts.

Phosphates may also be added in trace or, preferably, greater than trace amounts.

The general biotransformation process described herein using the aforementioned microorganism can be illustrated according to the following reaction scheme:

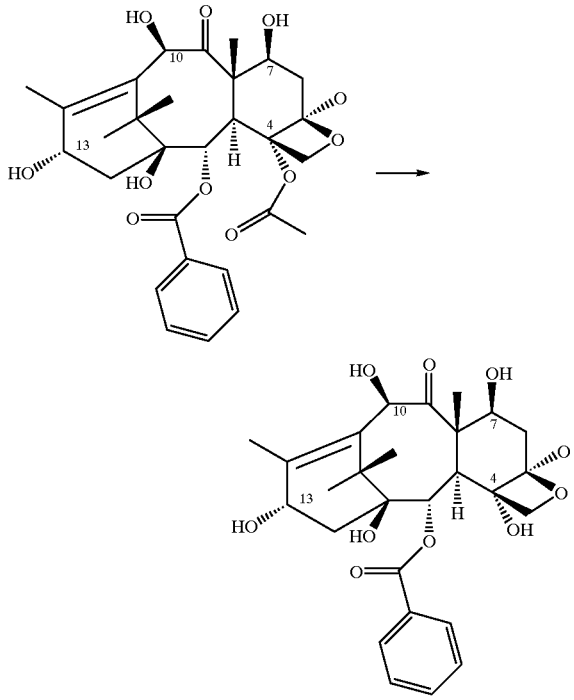

The specific examples that follow illustrate the synthesis of representative compounds of the instant invention and are not to be construed as limiting the invention in sphere or scope. The methods may be adapted to variations in order to produce intermediates and compounds embraced by this invention but not specifically disclosed. Further, variations of the methods to produce the same compounds in somewhat different fashion will also be evident to one skilled in the art.

EXAMPLE 1

Deacetylation of 10-deacetylbaccatin III

Medium: 0.5% toasted nutrisoy, 2% glucose, 0.5% yeast extract, 0.5% $K_2HPO_4$. 0.5% NaCl, adjusted to pH 7 with HCl (R. V. Smith and J. P. Rosazza, Arch. Biochem. Biophys., 161, 551–558 (1974)).

Strain SC16249 (ATCC 202192) isolated from a soil sample collected in Parsippany, N.J. was maintained on a plate containing the above medium plus 1.5% agar. 10 ml of the medium in a 50 ml flask was inoculated with a loopful of the culture. After 24 h incubation at 28° C., 200 rpm, the culture was centrifuged at 11951×g for 10 min. The cell pellet was resuspended in a 50 ml flask with 10 ml 50 mM potassium phosphate buffer, pH 7. 2 mg 10 deacetylbaccatin III dissolved in 0.2 ml methanol was added and the flask was shaken at 28° C., 200 rpm for 16 h. A sample of 0.7 ml was diluted with 0.7 ml methanol and analyzed by the HPLC method below. The molar yield of 4,10 dideacetylbaccatin III was 86%. HPLC retention time was the same as a chemically prepared standard. LC/MS analysis showed $(M+CH_3COO^-)^-=561$ indicating a molecular weight of 502.

HPLC method
column: Hewlett Packard Hypersil 5 (ODS C 18 200×4.6 mm)
mobile phase: 45% methanol; 55% water
flow rate: 1 ml/min
detection: 235 nm
temperature: 40° C.

TABLE 1

| Compound | ret. time min. |
|---|---|
| 10-deacetylbaccatin III | 10.221 |
| 4,10-dideacetylbaccatin III | 5.131 |

EXAMPLE 2

Deacetylation of 10-deacetylbaccatin III

Strains SC16249 (ATCC 202192) and SC 16250 (ATCC 202191) (both isolated from a soil sample collected in Parsippany, N.J.) were grown in 500 ml flasks containing 100 ml of the medium given in Example 1. The flasks were inoculated with a loopful of the culture and shaken for 64 h at 28° C., 200 rpm. Cells were collected by centrifugation, washed with 50 mM potassium phosphate buffer, pH 7, and centrifuged again. The cell pellets were resuspended at a concentration of 10% w/v in 50 mM potassium phosphate buffer, pH 7. Samples of cell suspension containing 2 mg 10-deacetylbaccatin III and 2%, 5%, 10% or 20% methanol in a total volume of 10 ml were shaken in 50 ml flasks at 28° C., 200 rpm. Samples of 0.5 ml were diluted with 0.5 ml methanol and analyzed by the HPLC method given in Example 1. The molar yield of 4,10-dideacetylbaccatin III was 96% after 2h for strain SC16249 (ATCC 202192) with 10% methanol. The molar yield of 4,10-dideacetylbaccatin III was 89% after 18h for strain SC16250 (ATCC 202191) with 5% methanol.

We claim:

1. A method for the preparation of 4-deacetyltaxanes, comprising the step of contacting a taxane with a microorganism of the genus Rhodococcus which deacetylates said taxane at the 4-position thereon to obtain 4-deacetyltaxane.

2. The method of claim 1, wherein said taxane is 10-deacetylbaccatin III, paclitaxel, cephalomannine, taxol c, 10-deacetylpaclitaxel, 10-deacetylcephalomannine, 7-β-xylosylpaclitaxel, baccatin-III, 7-β-xylosyl-10-deacetylcephalomannine, 7-β-xylosyl-10-deacetylbaccatin III, or 10-deacetyltaxol c.

3. The method of claim 1, wherein said 4-deacetyltaxane is 4,10-dideacetyl-baccatin III, 4-deacetylpaclitaxel, 4-deacetylcephalomannine, 4 deacetyltaxol c, 4,10-dideacetylpaclitaxel, 4,10-dideacetylcephalomannine, 4-deacetyl-7-β-xylosylpaclitaxel, 4-deacetylbbaccatin III, 4-deacetyl-7-β-xylosyl-10-deacetylcephalomannine, 4-deacetyl-7-β-xylosyl-10-deacetylbaccatin III, 4-deacetyl-7-β-xylosylbaccatin III, or 4,10-dideacetyltaxol c.

4. The method of claim 1, wherein said taxane is obtained by plant cell culture of, and/or extraction from plant tissue, wherein said plant is a member of the Taxus genus.

5. The method of claim 1, wherein said microorganism is Rhodococcus sp. ATCC 202192 (SC 16249) or Rhodococcus sp. ATCC 202191 (SC 16250).

* * * * *